US005672753A

United States Patent [19]

Drauz et al.

[11] Patent Number: 5,672,753
[45] Date of Patent: Sep. 30, 1997

[54] METHOD OF PRODUCING RACEMIC AMINO ALCOHOLS

[75] Inventors: Karlheinz Drauz, Freigericht; Wilfried Jahn, Gelnhausen; Michael Schwarm, Alzenau, all of Germany

[73] Assignee: Degussa Aktiengesellschaft, Germany

[21] Appl. No.: 603,554

[22] Filed: Feb. 21, 1996

[30] Foreign Application Priority Data

Feb. 21, 1995 [DE] Germany .................. 195 05 992.1

[51] Int. Cl.$^6$ .................................................. C07C 209/40
[52] U.S. Cl. ................................ 564/394; 564/468
[58] Field of Search .................................. 564/468, 394

[56] References Cited

U.S. PATENT DOCUMENTS 3,906,046  9/1975  Yoshida et al. .................. 260/584 R
3,979,457  9/1976  Fujii et al. ........................ 260/584 R

FOREIGN PATENT DOCUMENTS

0485069A1   5/1992   European Pat. Off. .
61-271258A  12/1986  Japan .

OTHER PUBLICATIONS

Atsushi Abiko et al.: "An Improved Convenient Procedure for Reduction of Amino Acids to Aminoalcohols: Use of NaBH$_4$ -H$_2$SO$_4$", Tetrahedron Letters, May 12, 1992, pp. 5517-5518.

R. Hemmer, et al.: "Reduktion von Oximen und Oxim-Derivaten zu Aminen", Houben-Weyl-Methoden der Organischen Chemie, vol. E16d, 1992, pp. 878-894.

C. Hoffman, et al.: "Synthesis Of Alpha-Amino Acids By Reduction Of Alpha-Oximino Esters With Titanium(III) Chloride And Sodium Borohydride", The Journal of Organic Chemistry, vol. 54, No. 15, Jul. 21, 1989, pp. 3750-3751.

M.J. McKennon et al.: "A Convenient Reduction Of Amino Acids And Their Derivatives", Journal of Organic Chemistry, vol. 58, 1993, pp. 3568-3571.

Y. Matsuda et al.: "Preparation of alpha-(N-Trimethylsilyl)imino Esters and Their Use In The Synthesis of Alpha . . . -ones", Journal of the Chemical Society, Perkin Transactions 1, 1989, pp. 279-281.

European Search Report dated 29 Apr. 1996.

*Primary Examiner*—Brian M. Burn
*Attorney, Agent, or Firm*—Cushman Darby & Cushman IP Group of Pillsbury Madison & Sutro

[57] ABSTRACT

α-oximino carboxylic acids or their esters are reduced with an alkali boron hydride and hydrogen chloride or sulfuric acid to yield racemic amino alcohols (e.g. (RS)-tert-leucinol).

10 Claims, No Drawings

METHOD OF PRODUCING RACEMIC AMINO ALCOHOLS

BACKGROUND OF THE INVENTION

1. Field of the Invention

The invention is relative to a method of producing racemic amino alcohols of general formula I

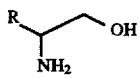    (I)

in which R1 can be a straight-chain, branched or cyclic alkyl-, arylalkyl- or aryl group with up to 20C atoms, which group can, in addition, contain heteroatoms such as O, N or S, by means of the reduction of α-oximino carboxylic acids or their esters of general formula III

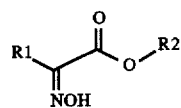    (III)

in which R1 has the meaning indicated above and R2 stands for hydrogen or an alkyl group with up to four C atoms.

2. Background Information

Racemic amino alcohols of general formula I are important intermediate products in the production of optically active amino alcohols obtainable from the racemic compounds by resolutions of racemates. The latter can be carried out either enzymatically (F. Francalani, P. Cesti, W. Cabri, D. Bianchi, T. Martinengo, M. Foà, J. Org. Chem. 1987, 52, 5079; S. Fernández, R. Brieva, F. Rebolledo, V. Gotor, J. Chem. Soc. Perkin Trans. I 1992, 2885; H. S. Bevinakatti, R. V. Newadkar, Tetrahedron: Asymmetry 1990, 1, 583), by preferred crystallization of the one enantiomer (K. Saigo, H. Miura, K. Ishizaki, H. Nohira, Bull. Chem. Soc. Jpn. 1982, 55, 1188) or classically by reacting with an optically active acid and fractionated crystallization of the diastereomeric salt pairs (DE 35 17 108 A1). The optically active amino alcohols obtained in this manner find many applications, e.g. in medicine or pharmacy as active substances or intermediate products as well as chiral inductors or catalysts in asymmetric synthesis. products as well as chiral inductors or catalysts in asymmetric synthesis.

The required racemic amino alcohols of general formula I can be obtained in various ways. Thus, racemic amino acids or their esters can be reduced with diverse hydridic reagents to the corresponding amino alcohols (A. Abiko, S. Masamune, Tetrahedron Lett. 1992, 33, 5517; M. J. McKennon, A. I. Meyers, K. Drauz, M. Schwarm, J. Org. Chem. 1993, 58, 3568 and the literature cited there).

In some instances, however, these compounds are not obtainable or not readily obtainable, e.g. in the case of (RS)-tert-leucine. It can then be advantageous to react α-keto carboxylic acids or their esters of general formula II, in which R1 has the meaning indicated above and R2 stands for hydrogen or a lower alkyl group with up to four C atoms, with hydroxylamine or one of its salts to form the α-oximino derivative of general formula III, in which R1 and R2 have the meanings indicated above, and

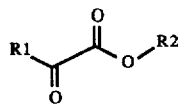    (II)

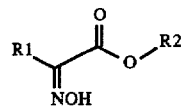    (III)

then reduce the latter hydridically to a racemic amino alcohol of general formula I (R. Schröter in: Houben-Weyl, Methoden der Organischen Chemie [German—"Methods of Organic Chemistry"], volume XI/1 (editor—E. Müller), p. 495 ff, Georg Thieme Verlag, Stuttgart 1957; R. Hemmer, W. Lürken in: Houben-Weyl, Methoden der Organischen Chemie, volume E16d (editor—D. Klamann), p. 878 ff, Georg Thieme Verlag, Stuttgart 1992). However, only lithium aluminum hydride is known as a reducing agent for this. This is not only expensive but also problematic with respect to safety regulations because of its ready flammability. In a similar reaction sequence α-keto carboxylic acid esters were converted into the corresponding α-(N-trimethylsilyl) imino esters, which were then likewise 2reduced with lithium aluminum hydride to the racemic amino alcohols (Y. Matsuda, S. Tanimoto, T. Okamoto, S. M. Ali, J. Chem. Soc. Perkin Trans. I 1989, 279).

SUMMARY OF THE INVENTION

A means was therefore sought of carrying out the reduction of readily producible α-oximino carboxylic acids or -esters of general formula III with a reduction agent which would be more advantageous in terms of expense and safety in order to be able to make available in this manner the racemic amino alcohols of general formula I in an easy, clean manner and with a good yield.

This problem is solved by a method of the initially mentioned type with the features detailed in claim 1. Further advantageous embodiments of the invention are recited in the dependent claims.

According to this method, the α-oximino carboxylic acids or -esters of general formula III are reduced easily, cleanly and in a good yield by means of reduction with an alkali boron hydride and sulfuric acid or also hydrogen chloride as activator in a solvent, to the racemic amino alcohols of general formula I.

In an especially preferred variant of the reaction, the α-oximino carboxylic acid derivative is placed in a receiver with the alkali boron hydride and then hydrogen chloride or sulfuric acid is added in order to activate the reduction reaction. In particular, economical sodium boron hydride, but also lithium boron hydride can be considered as alkali boron hydride in this connection. 2–5 (preferably 3–4) moles of the alkali boron hydride per mole of the α-oximino compound of general formula III are used for the reduction. It is advantageous to use 1 mole hydrogen chloride or ½ mole sulfuric acid for each mole alkali boron hydride for activation. The preferred solvents are ethers, especially those with a boiling point of below 90° C., especially 1,2-dimethoxyethane or tetrahydrofurane.

These reagents are already known for the reduction of amino acids (Abiko, Masumune 1992). It advantageously happened that they are also very well suited for the reduction of α-oximino carboxylic acids or -esters of general formula III to racemic amino alcohols of general formula I; the reaction takes place in principle within a broad temperature range from approximately −20° C. to the boiling temperature of the solvent used, but preferably in such a manner that the reagents are brought together approximately at room temperature under optional cooling and the reaction is then completed by heating to temperatures of up to approximately 75° C. This was especially surprising for the reason that the agent with the reducing action is obviously diborane produced in situ (Abiko, Masamune, 1992) because it has been pointed out elsewhere (H. Feuer, D. M. Braunstein, J. Org. Chem. 1969, 34, 1817) that oximes were able to be reduced to the corresponding amines by diborane only at an elevated temperature of 105°–110° C. in diethylene glycol dimethyl ether-THF whereas at 25°–65° C. no reaction or at 85°–90° C. only reduction to the corresponding hydroxyl amine was observed. In contrast thereto, for the reduction of α-oximino carboxylic acids or -esters of general formula III to racemic amino alcohols of general formula I carried out in accordance with the invention, such high temperatures and the use of the expensive solvent diethylene glycol dimethyl ether, which renders the workup difficult, can be surprisingly eliminated. On the contrary, it is even advantageous to use ethers with a boiling point of below 90° C. since (1) they are more economical, (2) the reduction can be carried out under relatively mild and protective conditions and (3) the solvent can be readily separated from the product by distillation within the framework of the workup.

After the end of the reaction the reaction mixture is hydrolyzed with an alcohol and/or water, the organic solvent distilled off, the residue taken up in water and rendered acidic with hydrochloric acid or another acid, agitated for a time and then rendered alkaline, preferably with sodium hydroxide solution. The racemic amino alcohol of general formula I is extracted with a suitable organic solvent and purified further after evaporation to low bulk, if necessary by distillation, chromatography or recrystallization, optionally of a salt.

On the whole, the method of the invention opens up a novel, especially simple access to racemic amino alcohols of general formula I by the reduction of α-oximino carboxylic acids or -esters of general formula III, which, for their part, can be readily produced from the corresponding α-keto acids or -esters of general formula II. The racemic amino alcohols of general formula I produced in accordance with the invention serve, among other things, as starting materials for resolutions of racemates which result in optically active amino alcohols.

DETAILED DESCRIPTION OF THE INVENTION

The invention is explained further in the following examples:

EXAMPLE 1

Production of trimethylpyruvic acid oxime 163 g (1 mole) 93.5% trimethylpyruvic acid sodium salt and 69.5 g (1 mole) hydroxylamine hydrochloride were dissolved at 40° C. in 450 ml water. The product crystallized out during slow cooling off under agitation. After 1.5 h agitation in an ice bath the crystals were filtered off, washed with 150 ml ice water and at first pre-dried in a vacuum at 60° C. and then post-dried in a vacuum desiccator over phosphorus pentoxide to constant weight. 117.8 g (yield 81%) trimethylpyruvic acid oxime in the form of colorless crystals were obtained.
Melting range: 120°–122° C. (decomposition) (lit.: 121° C. (F. Knoop, G. Landmann, Z. physiol. Chem. 1914, 89, 157))
$C_6H_{11}NO_3$ calc. C 49.64 H 7.64 N 9.65 (145.16) obs. C 49.75 H 7.89 N 9.71

EXAMPLE 2

Production of (RS)-tert-leucinol

First, 120 ml (2.25 moles) conc. sulfuric acid were added dropwise under agitation at a maximum of 15° C. to 480 ml 1,2-dimethoxyethane (DME).

218 g (1.5 moles) trimethylpyruvic acid oxime were added in portions to an agitated suspension of 171 g (4.5 moles) sodium boron hydride in 1500 ml DME at 10°–30° C., during which a vigorous development of gas began. Then the sulfuric acid-DME solution was added dropwise under ice cooling within 2.5 h, during which the temperature rose from 10° C. to 40° C. and, after removal of the cooling, to 55° C. The mixture was then heated to 70° C., cooled, and the batch allowed to stand for 2 days at room temperature.

In order to destroy excess boron hydride, first 200 ml methanol were added dropwise at 20°–55° C. and then 100 ml water, during which the temperature rose to 60° C. A vigorous development of gas was observed during the entire hydrolysis procedure. The mixture was then evaporated in a vacuum to a thin pulp and the organic solvent mixture distilled off after the addition of a further 500 ml ice water. After the addition of a further 600 ml water, 200 ml conc. hydrochloric acid were added dropwise at 25° C., during which the temperature rose to 35° C. and a vigorous development of gas began again.

After 15 min of post-agitation the suspension was compounded with 1500 ml toluene and alkalinized with 300 ml 50% sodium hydroxide solution. The temperature, which rose during this procedure to 55° C., was elevated further to 70° C., whereupon the toluene phase was separated. The aqueous phase was extracted twice again with 1 l toluene, each time at 70° C. The combined toluene phases were then treated with Celite, filtered and evaporated to dryness in a vacuum, yielding 158 g of a yellowish oil which crystallized in the cold. Distillation yielded 125.1 g (yield 71%) (RS)-tert-leucinol as a colorless liquid which solidified at room temperature. A $^1$H-NMR spectrum corroborated the suggested structure.
Boiling range: 86°–95° C./13 mbar
Melting range: 34°–35° C.
$C_6H_{15}NO$ calc. C 61.49 H 12.90 N 11.95 117.19 obs. C 61.10 H 13.15 N 11.88

EXAMPLE 3

Production of 2-hydroxyimino-4-phenyl butyric acid ethyl ester 103.14 g (0.5 mole) 2-oxo-4-phenyl butyric acid ethyl ester, 34.75 g (0.5 mole) hydroxylamine hydrochloride, 104 ml (0.75 mole) triethylamine and 500 ml ethanol were agitated overnight at room temperature. The batch was then evaporated to dryness and the residue taken up in 700 ml methyl-tert-butyl ether. After washing with 200 ml water, 200 ml 0.2N hydrochloric acid and 100 ml water, the organic phase was evaporated to dryness and the residue recrystallized after filtration from 170 ml toluene. 52.9 g (48%) 2-hydroxyimino-4-phenyl butyric acid ethyl ester were isolated in the form of colorless crystals. A $^1$H-NMR spectrum corroborated the suggested structure.
Melting range: 84°–85° C.

EXAMPLE 4

Production of (RS)-2-amino-4-phenyl-1-butanol ( (RS)-homophenyl alaninol)

33.2 g (0.15 mole) 2-hydroxyimino-4-phenyl butyric acid ethyl ester were steadily introduced under agitation into a suspension of 24.15 g (0.64 mole) sodium boron hydride in 200 ml 1,2-dimethoxyethane (DME). Within 1 h a solution of 17.2 ml (0.32 mole) conc. sulfuric acid in 60 ml DME was added dropwise thereto, during which the temperature was maintained at 20°–30° C. The mixture was subsequently heated slowly to 62° C., then agitated 5 h at this temperature and cooled overnight under agitation to room temperature. After a careful addition of 50 ml methanol the batch was evaporated to dryness, the residue taken up in 120 ml water and compounded with 25 ml conc. hydrochloric acid, during which a vigorous development of gas began. After the addition of 150 ml toluene the mixture was agitated until the end of the development of gas, then alkalinized with 35 ml 50% sodium hydroxide solution and heated to 60° C. The organic phase was separated and the aqueous phase extracted again with 80 ml toluene at this temperature. The combined organic phases were dried over sodium sulfate and evaporated. 25.0 g raw (RS)-2-amino-4-phenyl-1-butanol remained as residue in the form of a brownish, viscous oil. The structure was corroborated by a $^1$H-NMR spectrum.

References cited herein are hereby incorporated by reference.

Further advantages and embodiments of the invention result from the following claims.

What is claimed is:

1. A method of producing racemic amino alcohols of general formula I

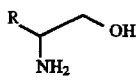 (I)

wherein R1 is a straight-chain, branched or cyclic alkyl-, arylalkyl- or aryl group with up to 20C atoms, comprising reducing α-oximino carboxylic acids or their esters of general formula III

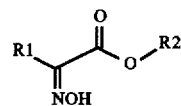 (III)

wherein R1 has the meaning indicated above and R2 stands for hydrogen or an alkyl group with up to four C atoms, wherein reduction is carried out with an alkali boron hydride in conjunction with hydrogen chloride or sulfuric acid as activator in a solvent.

2. The method of claim 1 wherein R2 is an alkyl, arylalkyl or aryl group which contains heteroatoms.

3. The method of claim 2 wherein the heteroatoms are selected from the group consisting of O, N and S.

4. The method according to claim 1, wherein the α-oximino carboxylic acid derivative and the alkali boron hydride are placed in a receiver and reduction is activated by adding hydrogen chloride or sulfuric acid.

5. The method according to claim 1, wherein sodium- or lithium boron hydride is used as alkali boron hydride.

6. The method according to claim 1 or 4, wherein an ether with a boiling point below 90° C. is used as solvent.

7. The method according to one of the claims 1–5, wherein the reaction is carried out between –20° C. and the boiling temperature of the solvent used.

8. The method according to claim 6, wherein the reaction is carried out between –20° C. and the boiling temperature of the solvent used.

9. The method according to one of claims 1–5, wherein the reaction mixture is hydrolyzed after the end of the reaction by adding alcohol, water and, optionally, an acid, the organic solvent distilled off, the aqueous phase then made alkaline and the racemic amino alcohol of general formula I is then extracted with an organic solvent and purified further after evaporation to low bulk, if necessary by distillation, chromatography or recrystallization, optionally of a salt.

10. A method of producing and optically active amino alcohol which comprises producing a mixture containing racemates of general formula I according to the method of one of claims 1–5 and resolving the racemates.

* * * * *